United States Patent
Kopp et al.

(10) Patent No.: US 10,463,771 B2
(45) Date of Patent: Nov. 5, 2019

(54) IMPLANT, COMPONENT SET, METHOD OF PRODUCING AN IMPLANT AND/OR A COMPONENT SET AND DEVICE FOR PRODUCING AN IMPLANT AND/OR A COMPONENT SET

(75) Inventors: Alexander Kopp, Aachen (DE); Ralf Smeets, Kreuzwertheim (DE)

(73) Assignee: MEOTEC GmbH & CO. KG (DE)

( * ) Notice: Subject to any disclaimer, the term of this patent is extended or adjusted under 35 U.S.C. 154(b) by 173 days.

(21) Appl. No.: 13/545,230

(22) Filed: Jul. 10, 2012

(65) Prior Publication Data

US 2013/0018480 A1  Jan. 17, 2013

(30) Foreign Application Priority Data

Jul. 11, 2011 (DE) .................. 10 2011 107 577

(51) Int. Cl.
*A61L 27/58* (2006.01)
*A61L 27/56* (2006.01)
*A61L 27/04* (2006.01)

(52) U.S. Cl.
CPC ............. *A61L 27/58* (2013.01); *A61L 27/047* (2013.01); *A61L 27/56* (2013.01); *Y10T 29/49826* (2015.01)

(58) Field of Classification Search
CPC .... A61F 2002/2835; A61F 2002/30011; A61F 2002/30032; A61L 27/58; A61L 27/56; A61L 27/04
USPC ...................... 623/16.11, 23.51, 23.53, 23.55
See application file for complete search history.

(56) References Cited

U.S. PATENT DOCUMENTS

| | | | |
|---|---|---|---|
| 4,964,801 A | 10/1990 | Kawahara et al. | |
| 2004/0049270 A1* | 3/2004 | Gewirtz | 623/17.11 |
| 2006/0246399 A1 | 11/2006 | Ehrl | |
| 2008/0090097 A1 | 4/2008 | Shaw et al. | |
| 2008/0103594 A1 | 5/2008 | Loffler et al. | |
| 2008/0140199 A1* | 6/2008 | Briest | A61L 27/58 623/17.11 |
| 2009/0081313 A1 | 3/2009 | Aghion et al. | |
| 2010/0016989 A1* | 1/2010 | Lyngstadaas et al. | 623/23.72 |
| 2010/0131052 A1* | 5/2010 | Kappelt | A61L 31/022 623/1.46 |
| 2010/0185299 A1 | 7/2010 | Nies | |
| 2010/0256773 A1* | 10/2010 | Thijs et al. | 623/23.55 |

FOREIGN PATENT DOCUMENTS

| | | |
|---|---|---|
| DE | 34 35 771 A1 | 4/1985 |
| DE | 36 39 030 A1 | 6/1987 |
| DE | 10 2004 036 954 | 3/2006 |
| DE | 10 2005 013 200 | 9/2006 |

(Continued)

OTHER PUBLICATIONS

WO 2010017959 A2 Translation.*

(Continued)

*Primary Examiner* — Brian A Dukert
(74) *Attorney, Agent, or Firm* — Tarolli, Sundheim, Covell & Tummino LLP (57) ABSTRACT

An implant includes a basic body made of magnesium or magnesium alloy. The implant has a microstructure and a macrostructure configured to enhance biochemical interaction between the implant and tissue with regard to degradation and ingrowth behavior.

18 Claims, 7 Drawing Sheets

(56) References Cited

FOREIGN PATENT DOCUMENTS

| | | |
|---|---|---|
| DE | 10 2010 008 781 | 8/2011 |
| GB | 2 148 122 A | 5/1985 |
| WO | 97/36708 A1 | 10/1997 |
| WO | WO 2006/077154 | 7/2006 |
| WO | WO 2008/064672 | 6/2008 |
| WO | WO 2010017959 A2 * | 2/2010 ......... A61B 17/0401 |

OTHER PUBLICATIONS

Nguyen et al., A Novel Manufacturing Route for Fabrication of Topologically-Ordered Porous Magnesium Scaffolds, Apr. 15, 2011 (published online), Advanced Engineering Materials, vol. 13, Issue 9, pp. 872-881.*

Hiromota et al., Control of degradation rate of bioabsorbable magnesium by anodization and steam treatment, Materials and Engineering C, 2010 pp. 1085-1093.*

Tan et al., Study on compression behavior of porous magnesium used as bone tissue engineering scaffolds, Biomedical Materials, 2009, pp. 1-7.*

German Search Report dated Mar. 8, 2012 in German Application No. 10 2011 107 577.5 with English translation of relevant parts.

Flott, Leslie W., The Challenge of Thickness Variation in Plating and Anodizing, Mar. 21, 2012, taken from https://www.materialstoday.com/metal-finishing/features/the-challenge-of-thickness-variation-in-plating on Jan. 24, 2018.

* cited by examiner

IMPLANT, COMPONENT SET, METHOD OF PRODUCING AN IMPLANT AND/OR A COMPONENT SET AND DEVICE FOR PRODUCING AN IMPLANT AND/OR A COMPONENT SET

CROSS REFERENCE TO RELATED APPLICATIONS

Applicant claims priority under 35 U.S.C. § 119 of German Application No. 10 2011 107 577.5 filed on Jul. 11, 2011, the disclosure of which is incorporated by reference.

BACKGROUND OF THE INVENTION

1. Field of the Invention

The invention relates to an implant, a component set, a method of producing an implant and/or a component set and a device for producing an implant and/or a component set.

2. Description of the Related Art

Numerous implants are familiar from the prior art. Implants have long been used to replace missing bones and to fix fractures. In maxillofacial surgery, for instance, bone defects as a result of accidents, deformations or tumour resections, for example, require extensive reconstruction. These medical measures are associated with high economic costs and are a burden on the health system.

Because of the required biological compatibility, the selection of implant materials in medical technology is small. Approaches to replacing missing bones with firm, i.e. resilient materials can roughly be divided into two groups: replacement with resorbable and replacement with non-resorbable implants.

Due to the hitherto unresolved problems in terms of the degradation behaviour as well as the products of breakdown of resorbable implants, non-resorbable implements made of surgical steels or titanium are currently standard. Titanium exhibits good durability, strength, corrosion-resistance and biocompatibility properties.

Nevertheless the implant remains a foreign body and has to be removed after a certain time due to inflammation, irritation or ageing. The revision operation again results in high costs and in turn increases the clinical risk. In addition, further operations constitute a severe detriment to the health of the patients, mean long periods of admission to hospital and working incapacity due to illness, resulting in an economic loss which cannot be underestimated.

Frequently there are also complications ranging as far as refractures, e.g. through load shielding in which the surrounding bone degenerates. Loosening of the implant through abrasive microsliding also occurs. Here too further invasive treatment measures are necessary.

Ultimately the comfort of the patients must also be taken into consideration. Patients often complain of discomfort as implants heat up in the sun or differences in the mechanical properties of the implant and bone cause problems.

For these reasons numerous attempts have been made to develop implants which can be absorbed by the body and converted into natural bone. This is possible through the transplantation of the patient's own bone for example. Here, bone is removed from the hip for instance and used elsewhere. However this procedure means a further surgical intervention, associated costs and risks and a weakening of the bone at the point of removal. Last but not least, autologous bone is only available to a limited extent and due to the different structure of the bone, cell necrosis often occurs in the poorly supplied interior of larger transplants.

Exogenous implants made of resorbable materials would on the other hand be unlimitedly available. However, due to the high requirements relating to biocompatibility, strength and degradation behaviour, such materials are hardly known. Polyactides (PLA) have already been in use for some time in medicine in the form of suture materials, screws and plates. They are biocompatible and degradable, but they break down in acidic form and exhibit limited mechanical parameters. In the form of films or plates the dense material often closes cavities in which inflammations and necrosis develop due to lack of transport mechanisms, resulting in severe complications.

In comparison with this biocompatible magnesium alloys exhibit almost optimum properties. As a mineral, magnesium is present in nearly all body cells and its alloys are considerably stronger than plastics. The low strength compared with titanium is in fact desirable as the mechanical strength and elasticity module of most magnesium alloys are comparable with those of human bone. Due to its unlimited biocompatibility and bone-like strength, magnesium as an endogenous component therefore fulfils all the prerequisites for an implant material. In spite of the good prerequisites and theoretical superiority of magnesium as an implant material, numerous research endeavors have so far not succeeded a developing a marketable magnesium implant. The spontaneous reaction of magnesium with water in a moist environment brings about a shift in the pH value and the release of hydrogen gas. The extremely dynamic conversion of magnesium thus leads to massive bubble formation (1 g Mg releases 1.03 l hydrogen gas). The consequences are irritation and inflammation as well as premature failure of the implant under loading. In addition, increase cell necrosis occurs in the interior of larger implants due to lack of supply to the cells.

For magnesium to make a breakthrough as an implant material it is therefore necessary to influence the degradation kinetics in such a way that the surrounding tissue has sufficient time to build up in-growing bone and to remove the otherwise biocompatible products of degradation. In order to achieve this numerous projects were initiated which had the aim of slowing the degradation of magnesium through influencing the alloy and the structure. However, to date it has not been possible to solve the degradation problem through the question of the material.

More recent approaches are aimed at influencing the resorption rate through modification of the marginal zone as part of mechanical compaction. This approach too has so far not provided satisfactory results.

A further method is the production of magnesium sponges by way of a gas release process in which chaotically arranged pores on the surface benefit the ingrowth behaviour of tissue. Despite good results with regard to this, the sponge structure actually breaks up excessively quickly. In addition, the unordered structure is less mechanically stable. In isolated cases overproportionally high pore densities in the components result in premature failure.

A new approach to controlling degradation is electrochemical conversion of the surface. Experiments have shown that by converting the surface as part of anodisation the degradation behaviour can be influenced. However, at present because of the previously described problems in the case of larger implant volumes this development is restricted to filigree structures.

SUMMARY OF THE INVENTION

The aim of the present invention is therefore to provide an improved implant.

In accordance with a first aspect of the invention, this is achieved by way of an implant with an implant body made of magnesium whereby implant body has a macrostructure.

Magnesium is taken to mean both pure magnesium as well as coated magnesium. Resorbable magnesium alloys are also covered.

The implant body can also be made of titanium. Titanium is taken to mean both pure titanium and coated titanium. The implant can then, more particularly, be designed as a permanent implant.

The macrostructure of the implant relates to its basic external design features. However this should not be understood as the three-dimensional form of the implant, but a structuring of the implant body in itself. More particularly, structures of the implant body which can be seen with the naked eye should be included. Preferably these structures can be regular.

The macrostructuring makes it possible to use magnesium with its unrestricted biocompatibility and bone-like strength as an implant material.

Preferably the macrostructure is in the form of channels. These can run continuously through the implant body. More particularly they can be arranged in a regular pattern and run in straight lines. However, irregular forms are also possible.

An implant design of this type has numerous advantages:

Firstly the newly formed bone tissue can be supplied with nutrients through the channels. Necrosis in the interior of the implant is prevented.

Secondly, in certain circumstances the total quantity of magnesium to be broken down by the body is reduced. At the same time this produces better mechanical strength and stability in the same way as in a framework structure.

Thirdly increased biochemical activity finally occurs during the bone healing process through a significant increase in the surface size.

In the case of a coating this leads to improved degradation behaviour due to a greater layer volume.

As a result, with a suitable configuration the resorption rate lies within the same or a similar range as the new bone formation so that no load shielding is necessary during the regeneration phase and in the ideal situation the defect is largely and possibly even fully healed with endogenous bone.

Other advantages include dispensing with the revision operation to remove the implant and the clinical risks associated therewith. Through the use of endogenous materials the inflammation and tolerability risk is also lower. Wearing comfort for the patient is also increased. Through increased social needs due to demographic developments the implant is in keeping with the times and is a response to overloading of the medical system. In addition to reducing the risk for the patient, pressure on the healthcare system is significantly relieved through dispensing with procedures.

The channels can run in one or more coordinate directions. More particularly they can run one or two-dimensionally. It is particularly preferable if the channels run in all three axial directions. This results in an interconnecting channel structure, similar to that found in natural bone. A frame-like implant body remains around the channels. In this way the supply of nutrients to the in-growing bone is further improved.

It is advantageous if the channels have a rectangular cross-section. In particular a square cross-section if possible. However, other cross-section forms such as a round or elliptical cross-section, or even asymmetrical cross-section forms are conceivable. The cross-sectional contour can also be superimposed with a special contour, for example in the form of waves or serrations.

The channels can have a width and/or height of approximately 100 to 1500 micrometers, preferably of 300 to 1000 micrometers, more particularly 500 to 700 micrometers. At the same time the wall thickness of the web remaining between the channels can also be varied in accordance with these dimensions. In this way the ratio of mass to surface area of the implant can be adjusted.

A further aspect of the invention relates to an implant in which the free surface of the implant is microstructured, whereby microstructuring is understood as a structuring of the surface which is no longer visible to the naked eye. For this the surface of the magnesium can be converted. More particularly, microstructuring of the surface of the magnesium can take place by way of a conversion process. A corrosion and wear resistant layer is produced which can be varied in terms of its roughness and porosity through suitable selection of the process parameters so that improved interaction with the surrounding tissue and in-growing bone cells takes place. The optimum conditions for microstructuring can be verified through biocompatibility tests. More particularly, the microstructure layer on the surface of the corrosive magnesium protects against premature disintegration in the moist environment in the body.

This occurs because of the greater resistance of the layer and the point by point use of layer corrosion in some circumstances, through which defects are produced that control the resorption of the basic material. In this way, by selecting the layer parameters the disintegration behaviour of the coated solid magnesium material can be adjusted.

Advantageously the surface can have more or more layers, more particularly a calcium phosphate layer and/or an oxide layer. The calcium phosphate layer can for example be hydroxylapatite or beta-tricalcium phosphate. The oxide layer can be magnesium oxide, for example. A layer of this type is typically produced during anodisation whereby the magnesium is oxidised. The oxide layer is firmly connected to the basic body. It reduces resorption. The above substances can also be present in mixed form in a layer. Any number of layers can also be present one behind the other in any combination. The last applied layer, i.e. the outermost layer can also comprise an organic coating or can contain such components, for example of conventional polymers (e.g. PDLLA, PGLA) and/or coupled molecules for optimising the cell niche, whereby cell adhesion molecules, cytokines (growth and differentiation factors) or viral and non-viral gene vectors (including plasmids) can be mentioned in particular.

This oxide layer can also be a ceramised layer as occurs during plasma chemical anodisation. This is even more stable and reduces resorption further.

Advantageously the surface has pores with a diameter of 0.1 to 50 micrometers, preferably from 2 to 5 micrometers. In this way the surface property can be varied. Improved interaction with surrounding tissue and in-growing bone cells takes place.

If microstructurng and suitable macrostructuring are combined the mass of the complete material can be reduced while the surface and the mass of the coating are increased. If, after having been in use in the body for a longer time, the layer has largely or fully disintegrated, only small islands of the basic substance remain which are already partially supported by the newly formed bone and in spite of increased resorption do not lead to an essential increase in the disintegration rate. In summary, combining microstructuring and macrostructuring has numerous advantages. In a suitable embodiment it is possible to produce a degradable implant from magnesium which breaks down evenly irrespective of its size and shape. Through the body-friendly and even dosage of the in other respects biocompatible products of breakdown, the otherwise usual complications are reduced. Ideally the implant retains its stability long enough to give the surrounding bone the time required for healing the defect.

A further aspect of the invention comprises a method of producing an implant and/or a component set for an implant, whereby in a first step macrostructuring and/or microstructuring take place. Thus, in a first step the structure can be produced which is visible to the naked eye. The production of the structures no longer visible to the naked eye can alternatively or cumulatively take place in a first step.

Advantageously the macrostructuring takes place by way of spark erosion (Electrical Discharge Machining, EDM) or by way of electrochemical machining (ECM). In his way the dimensional accuracy and surface quality can be assured.

By means of EDM or ECM an electrode can be sunk into one or more, for example, three, different planes in a magnesium basic body. The EDM or ECM treatment offers the necessary flexibility in terms of the channel geometry and makes the required aspect ratio possible.

Alternatively the shape can be produced by way of a generating method, for example Selective Laser Melting (SLM).

In a following step an individual implant is produced from the basic body on the basis of the clinical data of the patient. This either takes place by way of machining or through EDM or ECM. For this the patient data from imaging procedures are converted into production data.

Alternatively the external form is approximated or produced through joining components in accordance with a modular system. The components can preferably be supplied as a component set containing various basic shapes, for example, corners, curves, cubes, dice, rods etc.

To give the form mechanical stability the components can have grips, hooks, catches, clips, adhesive connections, welded connections or interlocking or friction connections in general, which complement each other. In this way through joining together the components contained in the component set a macrostructure for a basic body of an implant can be produced.

In a following step the implant can be coated. However, coating can also take place during the first step before shaping.

For this the surface can be treated by means of anodisation, whereby an ordered pore structure may possibly result. Through the electrochemical reaction on the surface of the implant the surface is converted/oxidised. The oxide layer does not only grow on the surface itself, but into the volume of the implant body. This results in excellent adhesion. The oxide layer grows in the form of pillars with central pores. Because of this the resorption rate of the coated implant is reduced.

Advantageously the surface can be treated by means of plasma chemical anodisation. This produces oxide layers, the resistance of which is again considerably increased. Plasma chemical processes take place in special electrolytes and at much higher electrical field strengths. Due to the high electrical field strength, which exceeds the breakthrough voltage of the forming oxide layer, local discharges occur. This results in local plasma through which at high temperature and pressure the oxide layer being produced is modified. Through this in a so-called ceramised surface is created and the resorption rate of the coated implant is reduced further.

For the plasma chemical anodisation an electrolyte can be used which comprises at least the following:
a. Ammonium hydroxide 25% (AH): 60 ml/l to 400 ml/l
b. Diammonium hydrogen phosphate (DAHP): 0.05 mol/l to 0.2 mol/l
and
c. Urea (U): 0 mol/l to 1 mol/l
more particularly around 48% DAHP, 37% U and 15% AH of these components at the same ratio to each other of the above maximum concentration, measured as volume % or weight %.

It is of advantage if the electrolyte has a pH value in the range 8-12, more particularly 9-11.

Advantageously, for ECM and plasma chemical anodisation a common electrolyte which is suitable for both processing steps, can be used in an installation which is also suitable for both steps. Here, the component is in the electrolyte and is poled as an anode during the entire duration of the process. Both the immersion electrode for ECM and also the cathode plates for the anodisation are poled as cathodes. During the electrochemical treatment counter-contacting takes place through the immersion electrode and during the anodisation through the cathode plates. Only the applied voltage, current and a signal course determine whether the surface of the workplace is anodically converted or the surface is anodically dissolved.

A further aspect of the invention comprises a device for producing an implant and/or a component set and/or for implementing a method. Advantageously the electrode is pre-structured for the EDM and/or ECM treatment.

BRIEF DESCRIPTION OF THE DRAWINGS

The invention will be described below with the aid of examples of embodiment and with reference to the drawings.

Herein

DETAILED DESCRIPTION OF THE PREFERRED EMBODIMENTS

Figure 1:
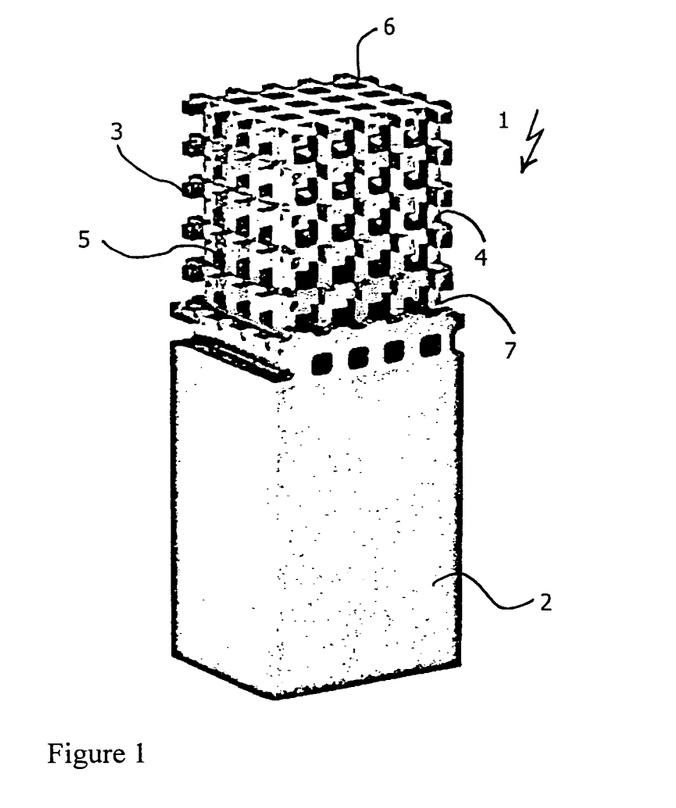
FIG. 1 show a schematic view of a macrostructured basic body.

In order to produce a macrostructured basic body 1, by way of spark erosion in all three spatial dimensions an implant basic body 3 structured by way of corresponding channels is eroded from a magnesium basic body 2. The resulting channels such as, for example 4, 5 and 6, in all three spatial directions form a three-dimensional interconnecting channel structure. The channels of the microstructure have a size of 500 to 700 micrometers. Walls, such as 7 for example, remain in place between them.

Figure 2A:
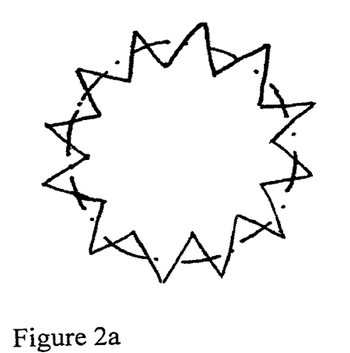
FIG. 2 shows schematic view of possible cross-section contours of the channels.
Figure 2B:
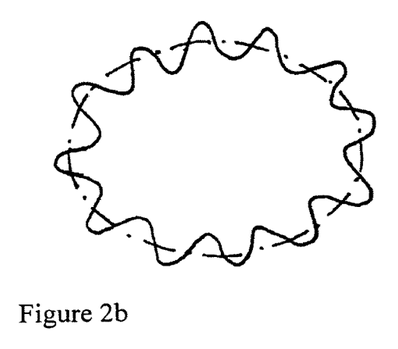
Figure 2C:
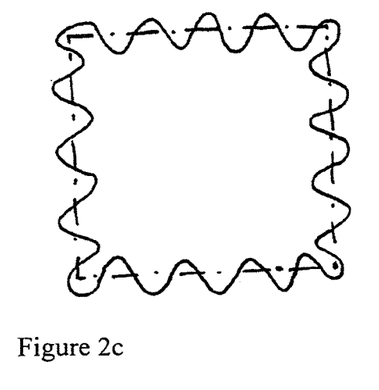
Figure 2D:
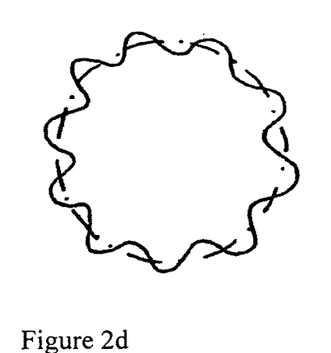
Figure 2E:
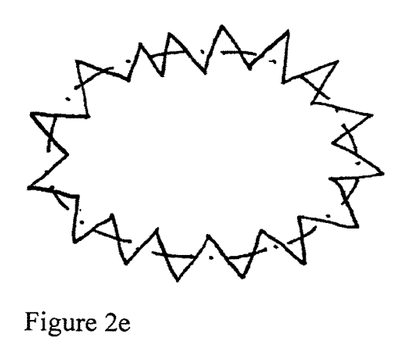
Figure 2F:
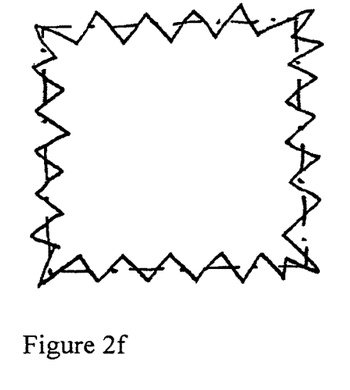

The cross-sectional contour of the channels can be overlaid with special contours. FIG. 2a shows a circular cross-section with an overlaid wave form, FIG. 2b shows an elliptical cross-section overlaid with a wave form, and FIG. 2c shows a rectangular cross-section overlaid with a wave form. FIG. 2d on the other hand shows a circular cross-section overlaid with a serrated contour, FIG. 2e an elliptical cross-section also overlaid with serrations, and FIG. 2f a quadratic cross-section also with a serrated overlay.

Figure 3A:
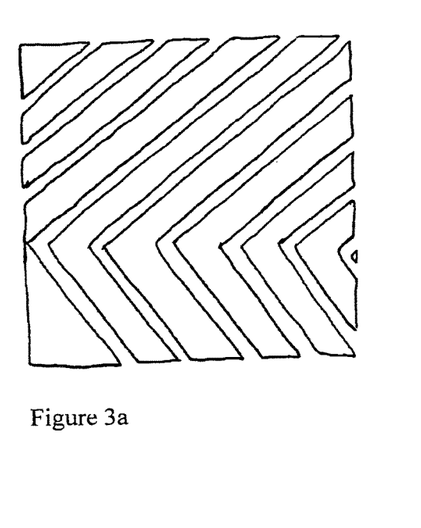
FIG. 3 shows schematic view of possible channel courses.
Figure 3B:
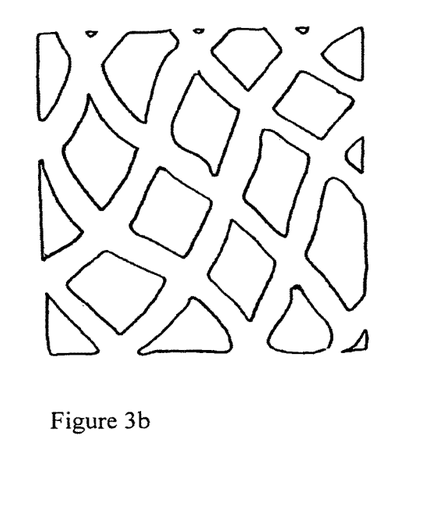
Figure 4:
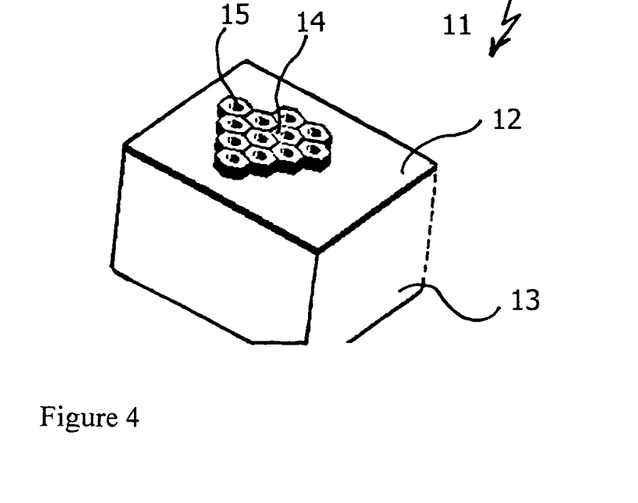
FIG. 4 shows a section from a microstructured surface.

Zigzag-shape channels as shown in FIG. 3a can be considered as possible channel courses. Completely irregular channel courses as shown in FIG. 3b are also possible.

For a basic implant body with a microstructured surface 11 as shown in FIG. 3 the surface of basic body 13 is anodised. This results in an oxide layer 14 with a regular surface structure, or in the case of plasma chemical anodisation, an oxide layer with an irregular surface structure (not illustrated). This has pores such as 15 for example. These measure 2 to 5 microns.

Figure 5:
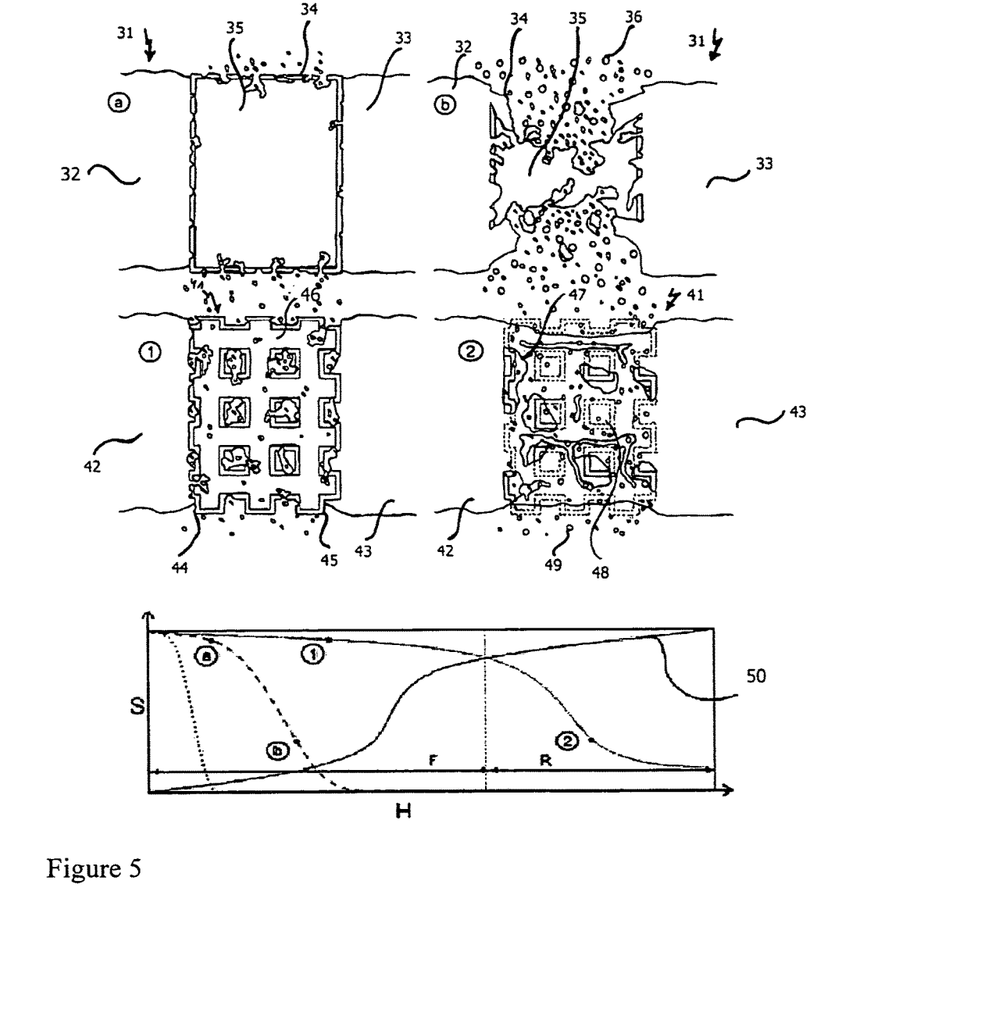
FIG. 5 shows the schematic degradation behaviour of coated magnesium implants and an implant design with micro and macrostructuring.

The letter a in FIG. 5, top left, denotes an implant of coated solid magnesium at the start of an incorporation process in two bone sections 32 and 33. The implant is coated with a corrosion and wear-resistant layer 34 which protect the magnesium basic body 35 against early disintegration in the moist environment of the body. After a certain time, with progression of the ingrowth process layer corrosion occurs and resorption of basic material sets in, which is shown by the letter b at the top right of the figure. In this way by selecting the layer parameters the disintegration of the coated solid magnesium 35 can also be positively influenced.

As the mass ratio of basic material is too great compared with the layer, only the initial increase in resorption rate is limited. There remains a solid body of magnesium corroding at an accelerating rate which fails early. Due to the large volume of solid magnesium, in addition to early implant failure, increased hydrogen formation comes about. This occurs in bubbles such as 36 for example.

For this reason the microstructuring is combined with suitable macrostructuring, cf. FIG. 2 centre. As shown here, this behaviour changes for a macro and microstructured implant 41. The course of ingrowth of the implant 41 in two bone sections 42 and 43 is also shown here, whereby the section on the right marked 1 shows the condition at the start of the ingrowth process and the section marked 2 shows the condition after a certain amount of time has elapsed. The implant 41 has a macrostructure in the form of channels such as 44 for example. Microstructuring of the surface has also taken place through the application of the layer 45.

Through incorporating channels such as 44 in all axial directions an interconnecting channel structure is formed, similar to that also found in natural bone. In this way the mass of the solid material 46 is reduced, while the surface and thereby the mass of the coating 45 is increased. In addition, the resulting channels such as 44 allow an improved supply of nutrients to the ingrowing bone 42 and 43 in the channels too. Once the coating 45 has essentially disintegrated after having been is use in the body for a longer period of time, only small islands of the basic material, such as 47, remain which are already partially supported by the newly formed bone, such as at point 48 for example, and in spite of increased resorption do not lead to an increase in the disintegration rate. More particularly, only small quantities of hydrogen are released in bubbles such as 49.

The diagram at the bottom of FIG. 5 shows the degradation behaviour of various implant concepts as a function of stability S against time, which is the healing phase H, whereby the healing phase H can be divided into the function phase F and resorption phase R. The first curve in the form of dots represents pure magnesium with a purity of 99.99%. Already at the start of the ingrowth phase the stability decreases very rapidly. There is therefore no adequate functionality. The dashed second curve shows the degradation behaviour of an implant made of coated solid material as already described in the upper part of FIG. 5. Time points a and b are assigned here. Here the stability is already increased, i.e. degradation takes place at a later point in time in the healing phase, but this still occurs too early in the function phase to guarantee adequate stabilisation. The third, continuous, curve shows the degradation behaviour of an implant design with micro and macro-structuring as shown in FIG. 5, centre. Here too the two time points 1 and 2 at the start of the ingrowth phase and after advanced ingrowth are shown. Through this it is clear that the stability can be considerably increased by the micro and macrostructuring. Degradation only takes place at a very late point in time as part of the resorption phase R. For the duration of the function phase F the stability of the implant is almost fully retained. Furthermore, the decrease in stability is synchronised with the increase in stability due to the newly formed bone. This is shown by line 50. Whereas the stability of the implant only decreases slightly in the function phase, the stability of the newly formed bone already increases significantly in the function phase F. In the resorption phase R, in which the stability of the implant with micro and macrostructuring decreases rapidly, the newly formed has almost attained its full stability. Ideally, through the coordinated decrease in the stability of the implant design and the increase in the stability of the newly formed bone, no phase of instability occurs in the period up to full resorption.

Figure 6:
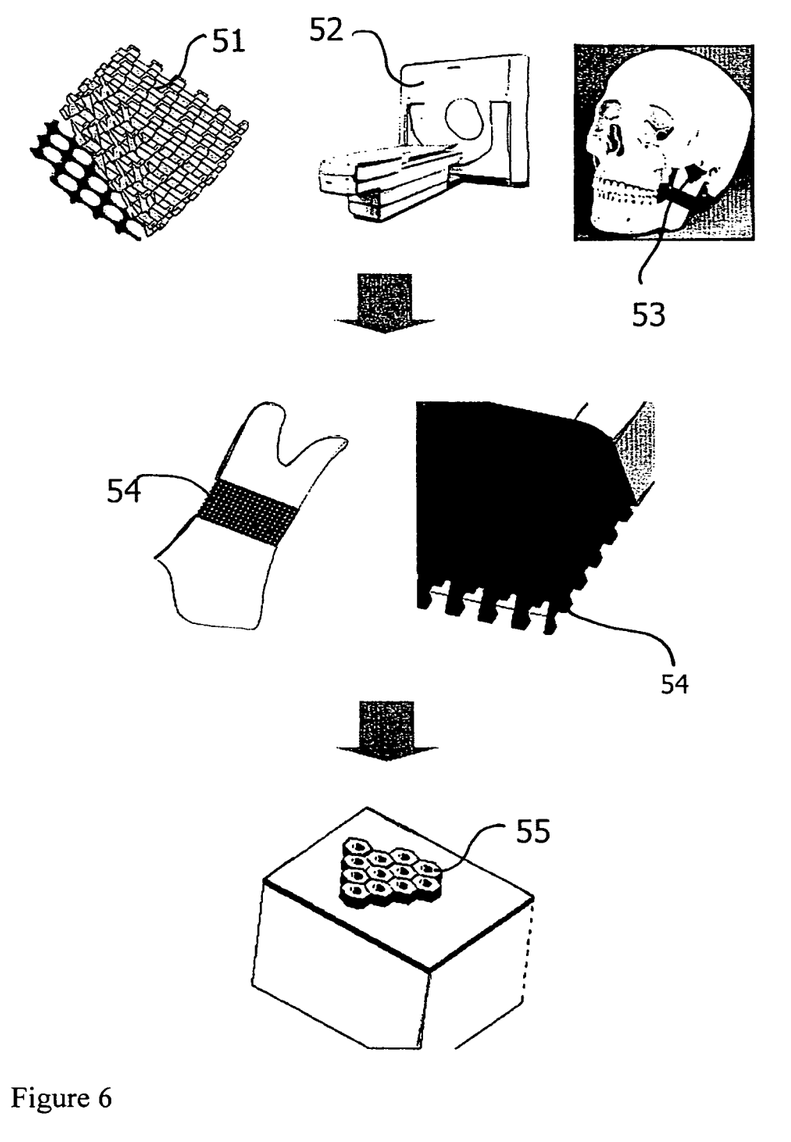
FIG. 6 schematically shows a production process for a jaw implant.

In order to be able to produce the desired structure of the implant, as shown in FIG. 6 the basic body is initially macrostructured and the implant structure 51 thus produced. On the basis of the clinical data relating to the defect, for example from computer tomography 52, CAD and CAM files 53 are created and adaptation of the primary material takes place. This results in an implant 54 which is individually matched to the defect. This then undergoes microstructuring in a coating process as shown schematically in 55.

Figure 7:
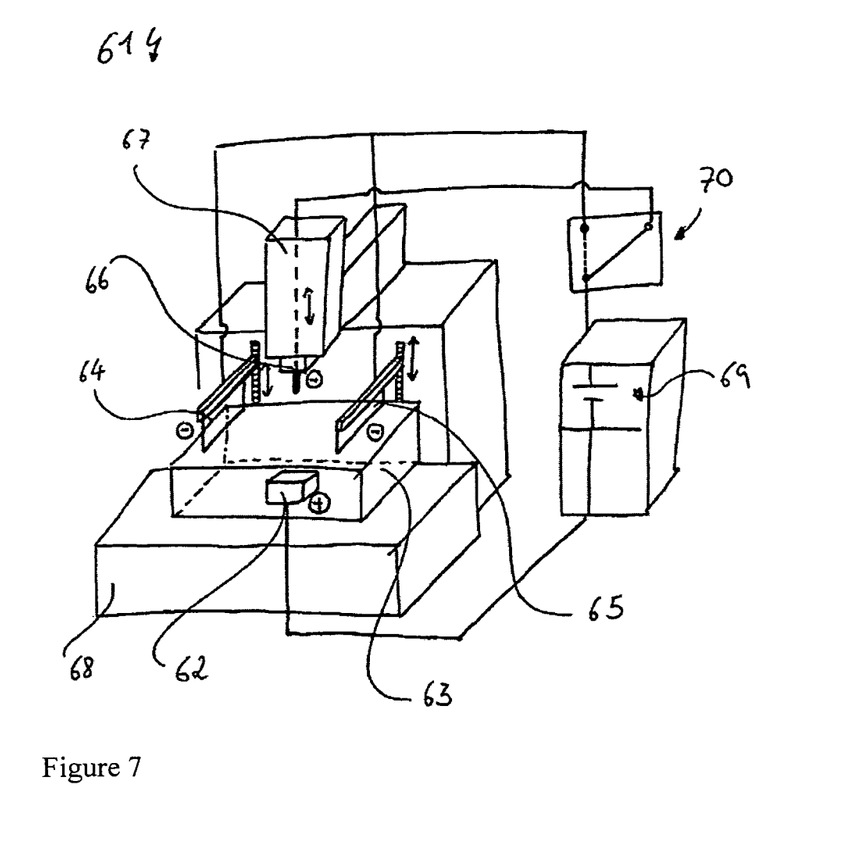
FIG. 7 schematically shows a production installation for ECM and plasma chemical anodisation.

In a production installation 61 ECM as well as plasma chemical anodisation can be carried out.

In the case of ECM the workpiece 63 is poled as an anode and is placed in any, though suitable for both processing steps, electrolyte (not shown) in an electrolyte bath 63. The cathode plates 64 and 65 are not in the electrolyte. The immersion electrode 66 on the sleeve 67 which is poled as a cathode is lowered into the electrolyte. On the basis of the set power parameters such as the level of current density and voltage, as well as the signal form, such as ramps, alternating current, unipolar pulsing, bipolar pulsing etc. the workpiece 62 is anodically dissolved. For this paths are travelled with the immersion electrode 66 as a result of which the external shape of the workpiece 62 is modified.

In the case of treatment by way of plasma chemical anodisation the workpiece 62 is again poled as an anode and is placed in any, though suitable for both processing steps, electrolyte. The immersion electrode 66 on the sleeve 67 is not on the electrolyte. The cathode plates 64, 65 are lowered into the electrolyte. On the basis of the set performance parameters such as the level of current density and voltage, as well as the signal form, such as ramps, unipolar pulsing, bipolar pulsing etc. the surface of the workpiece 62 is converted.

To increase the stability the production installation 61 has a machine frame 68. An energy supply 69 with a power source provides the necessary voltage via a switch 70 both for the cathode plates 64, 65 and for the immersion electrode 66. The power supply 69 also has a control device (not shown) with which the performance parameters can be controlled accordingly.

The invention claimed is:

1. Implant comprising:
   an implant body having a first implant body region, the first implant body region consisting of magnesium or a magnesium alloy,
   wherein the implant body has a macrostructure,
   wherein the macrostructure is in the form of channels,
   wherein the macrostructuring takes place through Selective Laser Melting,
   wherein a surface of the implant is microstructured,
   wherein the microstructured surface of the implant is affected by a conversion process, and
   wherein inner surfaces of the channels are microstructured.

2. Implant in accordance with claim 1, wherein the channels run in one or more axial directions.

3. Implant in accordance with claim 1, wherein the channels have a round, elliptical or rectangular cross-section.

4. Implant in accordance with claim 1, wherein the channels have a width and/or height of approximately 100 to 1500 μm.

5. Implant in accordance with claim 4, wherein the channels have a width and/or height of approximately 300 to 1000 μm.

6. Implant in accordance with claim 5, wherein the channels have a width and/or height of approximately 500 to 700 μm.

7. Implant in accordance with claim 1, wherein the surface has pores with a diameter of 0.1 μm to 50 μm.

8. Implant in accordance with claim 7, wherein the pores have a diameter of 1 μm to 10 μm.

9. Implant in accordance with claim 8, wherein the pores have a diameter of 2 μm to 5 μm.

10. Implant in accordance with claim 1, wherein the implant has components from a component set that are joined to each other.

11. Component set for joining components contained in the component set to produce a macrostructure for a basic body of an implant in accordance with claim 1.

12. Method of producing an implant in accordance with claim 1, the method comprising steps of:
    macrostructuring an implant body of the implant such that the implant body has channels, and
    microstructuring a surface of the implant via a conversion process, and
    microstructuring inner surfaces of the channels.

13. Implant in accordance with claim 1, wherein the conversion process comprises a conversion coating.

14. Implant in accordance with claim 1, wherein the conversion process comprises a wet coating process.

15. Implant in accordance with claim 1, wherein the microstructured surface of the implant comprises one or more layers containing phosphates and/or oxides.

16. Implant in accordance with claim 1, wherein the microstructured surface of the implant is affected by plasmachemical anodization.

17. Implant in accordance with claim 1, wherein a respective length of the channels is at least twice a respective width or diameter of the channels.

18. Implant in accordance with claim 13, wherein the macrostructure of the implant is affected by a generating method.

* * * * *